(12) United States Patent
Holloway et al.

(10) Patent No.: US 8,579,944 B2
(45) Date of Patent: Nov. 12, 2013

(54) BONE PLATE WITH SUTURE LOOPS

(75) Inventors: Ashley Holloway, Naples, FL (US); Joel Bales, Fort Myers, FL (US)

(73) Assignee: Arthrex, Inc., Naples, FL (US)

( * ) Notice: Subject to any disclaimer, the term of this patent is extended or adjusted under 35 U.S.C. 154(b) by 2093 days.

(21) Appl. No.: 11/396,554

(22) Filed: Apr. 4, 2006

(65) Prior Publication Data

US 2006/0241617 A1 Oct. 26, 2006

Related U.S. Application Data

(60) Provisional application No. 60/667,695, filed on Apr. 4, 2005.

(51) Int. Cl.
*A61B 17/80* (2006.01)

(52) U.S. Cl.
USPC .......................................................... 606/280

(58) Field of Classification Search
USPC ......... 606/280, 70, 71, 281–298, 68, 74, 232, 606/300
See application file for complete search history.

(56) References Cited

U.S. PATENT DOCUMENTS

| | | | |
|---|---|---|---|
| 5,735,875 A | 4/1998 | Bonutti et al. | |
| 5,785,713 A | 7/1998 | Jobe | |
| 6,093,201 A | 7/2000 | Cooper et al. | |
| 6,514,274 B1 | 2/2003 | Boucher et al. | |
| 6,520,965 B2 * | 2/2003 | Chervitz et al. | 606/74 |
| 2002/0052629 A1 * | 5/2002 | Morgan et al. | 606/232 |
| 2003/0050666 A1 * | 3/2003 | Grafton | 606/228 |
| 2005/0021033 A1 * | 1/2005 | Zeiler et al. | 606/70 |
| 2006/0259076 A1 * | 11/2006 | Burkhart et al. | 606/228 |

FOREIGN PATENT DOCUMENTS

EP 0 955 013 A1 11/1999

* cited by examiner

*Primary Examiner* — Sameh Boles
(74) *Attorney, Agent, or Firm* — Dickstein Shapiro LLP

(57) ABSTRACT

A bone plate and method of forming a bone plate having a plurality of suture loops pre-attached to the bone plate. The suture loops may be flexible and formed of a strong suture material. The suture loops may have various shapes, forms and configurations and may be provided on the bone plate in any number, depending on the characteristics of the fractured bone or bone segments, or of the plate design. Preferably, the suture loops are attached to a surface of the bone plate. The suture loops may receive a strand of suture for fixation of soft tissue to the bone plate.

24 Claims, 2 Drawing Sheets

BONE PLATE WITH SUTURE LOOPS

CROSS-REFERENCE TO RELATED APPLICATIONS

This application claims the benefit of U.S. Provisional Application Ser. No. 60/667,695, filed on Apr. 4, 2005, the entire disclosure of which is incorporated by reference herein.

FIELD OF THE INVENTION

The present invention relates to a bone plate system for fracture fixation and, more specifically, to a bone plate with suture loops that allow easy access for suturing and increased stabilization of the parts of the fracture.

BACKGROUND OF THE INVENTION

Fractured bones are often treated using fixation devices that reinforce the fractured bone and keep the fractured segments aligned during healing. The fixation devices may take a variety of forms, including casts for external fixation and bone plates for internal fixation. Bone plates are typically formed as rigid metal plates that are mounted on a fractured bone or bone segments to span or bridge the fracture. Typically, bones plate are held in place by screws or other fasteners attached to the bone on each side of the fracture through apertures in the bone plate.

Bone plates are considered the treatment of choice for many fractured bones, especially long bones, because they are compact, permitting an early return to motion. As illustrated in FIG. 1, in addition to screw holes (not shown) for affixing the plate to bone, bone plate 50 can be provided with through holes 57 and cutouts 52 that allow for the fixation to the bone plate of sutures attached to tubercules or other soft tissue. In this way, the bone plate can be used to tie down the tubercules or soft tissue. However, the holes 57 and cutouts 52 have sharp edges which increase the wear rate of the suture that is passed therethrough to tie down the soft tissue.

Accordingly, it would be desirable to provide a bone plate with a suture fastener that does not have any sharp edges. A bone plate with smooth edges which provide increased fixation strength of fractured bone, and with suture loops attached to the bone plate which provide additional fixation of associated soft tissue to the fractured bone and reliable suture connections, is also needed. A method of bone-tissue fixation using a bone plate with a suture fastener that does not have any sharp edges is further needed.

SUMMARY OF THE INVENTION

The present invention provides apparatus and methods for bone-tissue fixation using a bone plate having a suture fastener that does not have sharp edges. The bone plate of the present invention includes a body preferably formed of a metal and a plurality of suture loops which are pre-attached to the bone plate by themselves, a plastic material or by a fastening element. Preferably, the suture loops are flexible and formed of a strong suture material.

The present invention also provides a method of forming a bone plate having a suture fastener for surgical application. A plurality of suture loops are pre-attached to a bone plate by themselves, a plastic material or by a fastening element to maintain connection with the bone plate. Preferably, the suture loops are attached to a surface of the bone plate. The suture loops may have various shapes, forms and configurations and may be provided on a surface of the bone plate in any number, depending on the characteristics of the fractured bone or bone segments, or of the plate design. The suture loops preferably receive a flexible strand for fixation of tissue to the bone plate.

The present invention also provides a method for fixation of anatomical tissue during surgical applications by employing a bone plate having a suture fastener that does not have any sharp edges and a plurality of suture loops which are pre-attached to a surface of the bone plate. The method comprises the steps of: (i) providing a bone plate that includes at least one suture loop pre-attached to a surface of the bone plate; and (ii) surgically fixating anatomical tissue using the at least one suture loop.

Other features and advantages of the present invention will become apparent from the following description of exemplary embodiments of the invention with reference to the accompanying drawings.

DETAILED DESCRIPTION OF THE INVENTION

The present invention provides a bone plate having a plurality of suture loops which are pre-attached to the bone plate. Preferably, the suture loops are flexible and formed of a strong suture material. The invention also provides a method of forming a bone plate by providing suture loops pre-attached to a surface of the bone plate by themselves, a plastic material or by a fastening element to maintain connection with the bone plate. The suture loops may have various shapes, forms and configurations and may be provided on a surface of the bone plate in any number, depending on the characteristics of the fractured bone or bone segments, or of the plate design. The suture loops preferably receive a flexible strand, for example a suture strand, for fixation of tissue to the bone plate.

Figure 1:
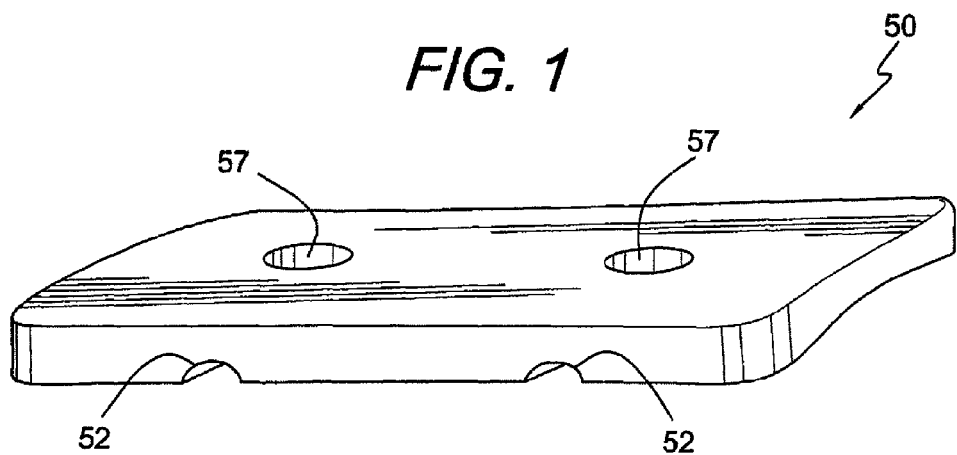
FIG. 1 illustrates a perspective side view of a section of a bone plate of the prior art illustrating sharp edges and cutouts on the side of the bone plate.
Figure 2:
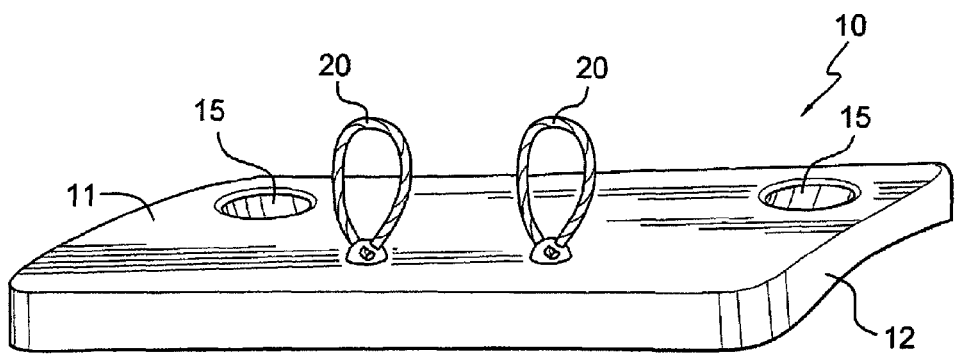
FIG. 2 illustrates a perspective side view of a section of a bone plate according to an embodiment of the present invention.
Figure 3:
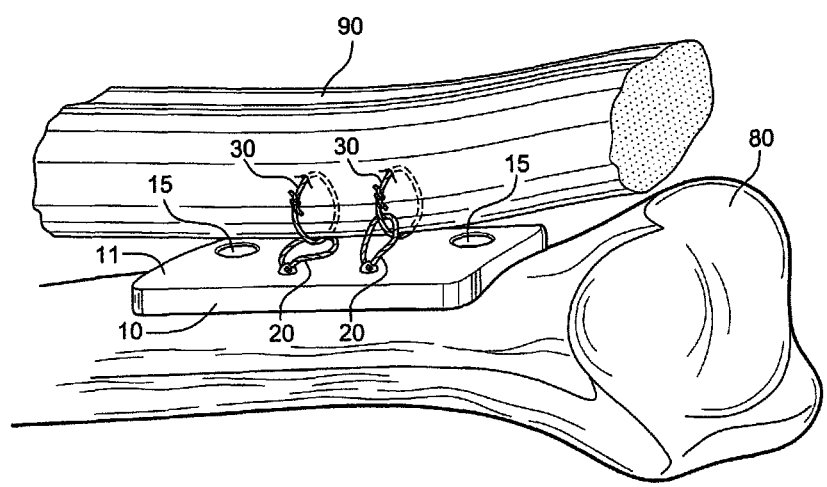
FIG. 3 illustrates the section of the bone plate of FIG. 2 undergoing additional bone-tissue fixation in accordance with a method of the present invention.

Referring now to the drawings, where like elements are designated by like reference numerals, a perspective side view of an exemplary bone plate 10 of the present invention is shown in FIGS. 2 and 3. For exemplary purposes only, the bone plate 10 is illustrated and described below as a bone plate for providing fixation of fractured humerus or of fractured humerus segments. However, the invention has applicability to the fixation of other bones or bone segments, including the fixation of associated soft tissue to bones or bone segments.

As shown in FIG. 2, the bone plate 10 includes a body 12 preferably formed of a metal such as titanium, titanium alloy, stainless steel, or other materials that possess mechanical and physical properties suitable for coupling bones together. The body 12 of the bone plate 10 is provided with a plurality of through holes or openings 15 that receive corresponding screws to secure the bone plate to bone. Openings 15 may be provided in any number and may have similar or different perimeters. Openings 15 may be also optimally placed in the body 12 of the bone plate and at various angles with respect to a transversal axis of the bone plate 10. In this manner, the bone plate 10 may be employed with angularly oriented screws, for example, to enhance the grip in more complex fractures, even in osteoporotic bone, and to ensure good fixation of the tissue to bone.

As shown in FIGS. 2 and 3, the bone plate 10 includes a plurality of suture loops 20 which are pre-attached to upper surface 11 of the bone plate 10, the upper surface 11 being oriented away from the fractured humerus. Sutures loops 20 extend from the upper surface 11 of the bone plate 10 and are attached to the surface 11 by a plastic material, for example by a heat bondable material, or by a fastening element, to maintain connection with the bone plate. Preferably, the suture loops 20 are flexible and are formed of a strong suture material known in the art, such as FiberWire suture, sold by Arthrex, Inc. of Naples, Fla. The suture loops 20 may have the same or different perimeter and may be provided in various forms and configurations. In addition, the suture loops 20 may be provided on the upper surface 11 in any number, depending on the characteristics of the fractured bone or bone segments, or of the plate design. As explained below, the suture loops 20 receive a flexible strand 30 for fixation of tissue to the plate.

The present invention also provides a method for fixation of anatomical tissue during surgical applications by employing bone plate 10 having a plurality of suture loops 20 which are pre-attached to surface 11 of the bone plate. The method comprises the steps of: (i) providing bone plate 10 having at least one suture loop 20 pre-attached to a surface of the bone plate in the vicinity of anatomical tissue 80, 90 to be affixed; and (ii) surgically fixating anatomical tissue 80, 90 using the at least one suture loop 20.

In an exemplary embodiment and referring to FIG. 3, the method of bone-tissue fixation using the bone plate 10 of the present invention includes the steps of (i) providing bone plate 10 adjacent the fractured bone fragments 80 and the associated soft tissue 90; (ii) fixating bone plate 10 adjacent the fractured bone fragments 80 by, for example, turning screws into bone 80 through holes 15 in the plate; (iii) once the bone plate 10 is secured against the fractured bone segments, advancing a strand 30, for example a suture strand, through the suture loops 20; and tying down soft tissue 90 using strand 30. In this manner, additional fixation of soft tissue to the fractured bone and additional fracture stabilization is provided, without decreasing the strength of the suture strand 30. The additional suture fixation neutralizes muscle tension, for example, and helps to maintain full range of motion during the healing process without pain. The material for the suture loops 20 may be similar to or different from that of the strand 30. In addition, one or a plurality of strands 30 may be attached to each suture loop 20. Both the suture loops 20 and flexible strands 30 may be formed of a strong suture material known in the art, such as FiberWire suture, sold by Arthrex, Inc. of Naples, Fla. At least one of the suture loops 20 and the flexible strands 30 may comprise a core of twisted fibers of ultrahigh molecular weight polyethylene. In addition, at least one of the suture loops 20 and the flexible strands 30 may be bioabsorbable.

Although the above-detailed embodiment has been described with reference to the fixation of bone plate 10 adjacent the fractured bone fragments by turning screws into bone through holes 15 in the plate and prior to the step of securing the soft tissue to bone, the invention is not limited to this embodiment. Accordingly, the invention also contemplates the use of suture anchors or other fixation devices in lieu of the screws. In certain embodiments and depending on a particular application, for example, the step of securing the soft tissue may be conducted prior to the step of fixating the bone plate to the fractured bone segments. In yet other applications, the step of securing the soft tissue may be conducted by (i) advancing the suture strand 30 through the tissue and not wrapping it around the soft tissue, as described above; and (ii) subsequently securing the suture strand by knot tying, for example. The suture loops 20 may be also employed for securing soft tissue without the suture strands 30. If desired, at least one of the suture loops 20 may be employed in conjunction with at least one suture strand 30, while other suture loops 20 may be employed without additional suture strands.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A bone plate, comprising:
   a body having a first surface and a bone-contacting surface; and
   at least one flexible suture loop formed of a flexible material, the at least one flexible suture loop being pre-attached, non-slidably, to the first surface of the bone plate.

2. The bone plate of claim 1, wherein the at least one suture loop is formed of a high strength suture material.

3. The bone plate of claim 1, wherein the at least one suture loop is attached to the first surface by a plastic material.

4. The bone plate of claim 1, wherein the at least one suture loop is attached to the first surface by a fastener.

5. The bone plate of claim 1 further comprising a plurality of suture loops, wherein at least one of the plurality of suture loops has a perimeter which is about equal to that of another of the plurality of suture loops.

6. The bone plate of claim 1, further comprising at least one aperture passing through the plate.

7. The bone plate of claim 1 further comprising at least one aperture passing through the first surface and through the bone-contacting surface.

8. The bone plate of claim 7, wherein the aperture accommodates a screw, an anchor or a washer.

9. The bone plate of claim 1 further comprising at least one flexible strand attached to the at least one suture loop, the flexible strand providing fixation of soft tissue to bone.

10. A plate suture assembly for treating a fracture of a bone, comprising:
    a bone plate positioned proximate to the bone, the bone plate comprising a plurality of flexible suture loops non-slidably secured to a surface of the bone plate that is proximate to soft tissue; and
    at least one suture strand attached to at least one of the plurality of flexible suture loops, the suture strand securing the soft tissue to the bone.

11. The plate suture assembly of claim 10, wherein the bone is humerus.

12. The plate suture assembly of claim 10, wherein at least one of the plurality of suture loops has a first perimeter and at least another of the plurality of suture loops has a second perimeter.

13. The plate suture assembly of claim 12, wherein the first perimeter is about equal to the second perimeter.

14. The plate suture assembly of claim 12, wherein the first perimeter is different from the second perimeter.

15. The plate suture assembly of claim 10, wherein the suture strand is positioned around the soft tissue.

16. The plate suture assembly of claim 10, wherein the suture strand is positioned through at least a portion of the soft tissue.

17. The plate suture assembly of claim 10, wherein at least one of the suture loops and the suture strand comprises a core of twisted fibers of ultrahigh molecular weight polyethylene.

18. The plate suture assembly of claim 10, wherein at least one of the suture loops and the suture strand is bioabsorbable.

19. A method of treating a fracture of a bone, comprising the steps of:
   providing a bone plate having a plurality of flexible suture loops pre-attached, non-slidably, to a surface of the bone plate by a plastic material or a fastener;
   positioning the bone plate proximal to a fracture of a bone; and
   securing the bone plate to the bone.

20. The method of claim 19 further comprising the steps of:
   passing at least one flexible strand through at least one of the plurality of suture loops; and
   securing the at least one flexible strand to a soft tissue.

21. The method of claim 20, wherein the step of securing the at least one flexible strand to the soft tissue further comprises providing the flexible strand around at least a portion of the soft tissue.

22. The method of claim 20, wherein the step of securing the at least one flexible strand to the soft tissue further comprises providing the flexible strand through at least a portion of the soft tissue.

23. The method of claim 19, wherein the step of securing the bone plate to the bone further comprises the steps of:
   providing at least one through-hole through the bone plate; and
   securing a fixation device through the through-hole and into the bone.

24. The method of claim 23, wherein the fixation device is selected from the group consisting of a washer, a screw and an anchor.

* * * * *